(12) United States Patent
Brady et al.

(10) Patent No.: US 7,331,349 B2
(45) Date of Patent: Feb. 19, 2008

(54) METHOD AND DEVICE FOR THE PREVENTION OF SNORING AND SLEEP APNEA

(75) Inventors: Patrick Raymond Brady, Dallas, TX (US); Gerhard Emil Maale, Dallas, TX (US); Holly Neville, Sunnyvale, TX (US)

(73) Assignee: Surgical Devices, Ltd., Co. Morningstar Holding Ltd., Charleston, Nevis, West Indies ( * ) Notice: Subject to any disclaimer, the term of this patent is extended or adjusted under 35 U.S.C. 154(b) by 696 days.

(21) Appl. No.: 10/349,820

(22) Filed: Jan. 23, 2003

(65) Prior Publication Data

US 2004/0144391 A1 Jul. 29, 2004

(51) Int. Cl.
*A61F 5/56* (2006.01)
(52) U.S. Cl. ...................... 128/848; 602/902
(58) Field of Classification Search ............... 128/845, 128/846, 848, 857–862; 602/902
See application file for complete search history.

(56) References Cited

U.S. PATENT DOCUMENTS

| | | | | |
|---|---|---|---|---|
| 3,709,228 A | * | 1/1973 | Barker | 607/139 |
| 4,034,474 A | * | 7/1977 | Lee | 433/69 |
| RE31,615 E | * | 6/1984 | Lee | 433/73 |
| 4,578,083 A | * | 3/1986 | Williams | 623/42 |
| 4,856,089 A | * | 8/1989 | Horton | 455/351 |
| 4,954,815 A | * | 9/1990 | Delmonte | 600/595 |
| 5,263,204 A | * | 11/1993 | Butsch | 2/424 |
| 5,361,416 A | * | 11/1994 | Petrie et al. | 2/171.2 |
| 5,687,743 A | * | 11/1997 | Goodwin | 128/848 |
| 6,315,743 B1 | * | 11/2001 | Guest | 601/134 |
| 6,468,238 B1 | * | 10/2002 | Hawkins et al. | 602/17 |
| 6,526,982 B1 | * | 3/2003 | Strong | 128/848 |

* cited by examiner

*Primary Examiner*—Michael A. Brown
(74) *Attorney, Agent, or Firm*—David W. Carstens; Carstens & Cahoon, LLP

(57) ABSTRACT

Snoring and sleep apnea are prevented by advancing the mandible of an individual during sleep. Instead of using an intra-oral device that has the potential to cause movement of the teeth, an extra-oral device is used, having a rigid headpiece, mandibular cradles that press against the posterior angle of the mandible, and a connector between the headpiece and the jaw pads to cause the force that maintains the mandible in the forward position to be transmitted to the head, rather than the teeth.

2 Claims, 12 Drawing Sheets

METHOD AND DEVICE FOR THE PREVENTION OF SNORING AND SLEEP APNEA

BACKGROUND OF THE INVENTION

1. Technical Field of the Invention

The present invention relates to an apparatus and method for treating snoring, with or with without sleep apnea. More specifically, the invention relates to an extra-oral method of providing mandibular advancement, a method shown to be effective in the treatment of snoring.

2. Background of the Invention

The term snoring generally refers to a rough or hoarse sound that arises from a person's mouth while sleeping. The problems caused by snoring are both social, affecting those who sleep with or near the person snoring, and medical, sometimes signaling a more profound problem known as sleep apnea.

FIG. 1B is a view looking into the mouth and demonstrates some of the portions of the mouth and pharynx (throat) that are involved in snoring. The tongue 103 takes up the visible area in the lower part of the mouth. The palate is the roof of the mouth and includes the hard palate 107, in which tissue closely overlies bone, and the soft palate 108, which has no underlying bones. The pendulous structure on the lower edge of the soft palate is the uvula 104. Two "arches" across the entrance to the throat are seen; the muscles that form these arches are the palatoglossus 110, which joins the palate and the tongue, and the palatopharyngeus 112, which joins the palate and the pharynx. The back of the pharynx 114 is seen behind the uvula, while the palatine tonsils 116 are seen bilaterally between the two arches. All of these structures, with the exception of the hard palate, are unsupported by bone along much of their length. During waking hours, normal tension in the muscles of the mouth and pharynx maintains a smooth airway in which air flows quietly, but as we fall asleep, these muscles become deeply relaxed. This can cause narrowing of the pharyngeal airway, which in turn causes turbulent airflow. This turbulent airflow vibrates the soft parts of the pharyngeal passage, causing the phenomenon we know as snoring. In children, enlarged tonsils or adenoids that obstruct the pharyngeal passageway can cause snoring. In adults, the contributing factors generally include a lack of muscle tone in the muscles of the airway, the consumption of alcohol or drugs, which causes a deeper relaxation, and smoking, which irritates the mucus membranes of the upper airway causing swelling and increased mucus production. Anatomical features can also play a part, such as a short neck or receding jaw line.

FIG. 1A shows a cross-section through the midline of a human head, showing the maxilla (upper jaw) 120, the mandible (lower jaw) 122, nasal airway 101, oral airway 102, tongue 103, hard palate 107, soft palate 108, uvula 104 and rear wall of the pharynx 114. Note especially that the tongue 103 has no fixed attachment other than to the back side of the mandible 122. (The tongue is also attached to the small hyoid bone 124, but this bone is not fixed.) This drawing makes it clear how little space exists between the rear wall of the pharynx 114 and the tongue 103, soft palate 108, and uvula 104. In a wakeful person, normal muscle tension maintains both the oral airway 102 and the posterior portions of the nasal airway 101 open to the trachea 107, and thus to the lungs. However, it is not difficult to imagine from this illustration what can happen when a person sleeps, especially if they sleep on their back. Given the effects of muscle relaxation and gravity, both the soft palate 108 and the rear portion of the tongue 103 can easily fall against the back of the pharynx 105. Depending on the degree of blockage, there can be simple snoring or a momentary, total blockage of the airflow, known as obstructive sleep apnea. Obstructive sleep apnea is a potentially very serious condition. The oxygen starvation it induces can cause the person to partially awaken in order that muscle tension can open the airway and get air into their lungs. Apnea patients may experience 30 to 300 obstructed events per night, and many spend as much as half their sleep time with blood oxygen levels below normal. During their obstructive episodes, the heart must pump harder to circulate the blood faster. This condition can cause excessive daytime sleepiness, irregular heartbeats, and after many years it leads to elevated blood pressure and heart enlargement. Persons with obstructive sleep apnea may spend little of their nighttime hours in the deep sleep stages that are essential for a good rest. Therefore, they awaken un-refreshed and are sleepy much of the day. They can even fall asleep while driving or performing other activities.

The prior art is replete with different efforts to attempt to control snoring and sleep apnea. Among the less intrusive methods of preventing snoring are special pillows, nasal strips, wrist alarms and chemical sprays. The shaped pillows have been designed to realign the back and spine and to relieve muscle stress during sleep, while the adhesive nasal strips help open the nostrils of a sleeper to improve breathing. Wrist alarms are designed to detect the noise of snoring and to partially arouse a sleeper, ideally to prompt the person to move to a less troublesome position. Chemical sprays contain oils and glycerin that can coat the mucus membranes of the pharyngeal passageway and decrease the noise associated with snoring. For mild cases, these remedies may be all that is necessary, or relief may be found by reducing triggering factors, i.e., losing weight, stopping smoking, and/or decreasing alcohol consumption. However, for more severe cases, the easy solutions usually do not solve the problem. The sleeper can shift and move off of a pillow, while the nasal strips will not help an obstruction in the pharynx. A wrist alarm does not allow the wearer to get a good night's sleep and chemical sprays can wear off in a few hours.

For more serious cases, and especially where sleep apnea is involved, the options have included Continuous Positive Airway Pressure (CPAP), mouth guards that reposition the lower jaw, and surgery.

CPAP uses a small compressor to create and maintain a positive pressure in the airway at all times by air forced through a nasal mask or nasal pillows. This positive pressure is enough to hold the airway open. The downside is that the mask must be firmly held in place on the patient's nose, while tubing ties the sleeper to the compressor. FIG. 2 shows a sleeping person wearing a nasal pillow connector 210 with attached tubing 212 that leads to a CPAP machine (not specifically shown). Various straps 214 hold the nasal pillows in place and the mouth closed. The masks or nasal pillows can cause skin irritation and pressure points, which in turn can be painful and can make falling asleep difficult. Although CPAP works well in persons who can tolerate it, not everyone can.

Surgical intervention is generally aimed at removing excess tissue in the pharynx or soft palate, such as tonsils, adenoids, and portions of the soft palate or uvula. Newer procedures have included a process to stiffen the tissue of the soft palate, so that it is less apt to form an obstruction.

At least one surgical procedure has taken a different tack to correct snoring, as is demonstrated in FIG. 3. An incision is made adjacent the anterior mandible 300, a portion of which is shown with the six anterior teeth 310. A small rectangular section 302 of the mandible is sectioned and pulled forward, with muscles of the tongue (the attachment can be seen in FIG. 1B) still attached. The section 302 is then rotated 90° and fixed in place. Because the muscles remain attached to the bony section, the body of the tongue is pulled to a more anterior position by several millimeters. This prevents the tongue from being able to move as far back into the pharynx as it was previously able to, increasing the airway and decreasing or eliminating snoring and apnea. While this surgery avoids the problem of the tongue blocking the airway, many sufferers consider surgery a rather drastic step, as it is often both expensive and painful.

Special dental mouthpieces can act in much the same way as the surgical procedure described above, but without the need to cut tissue. These mouthpieces reposition the lower jaw to a more forward position during sleep, preventing the tongue from obstructing the pharynx. The following figures demonstrate this repositioning of the bony structures of the jaws.

FIG. 4A is a model of a human skull, showing the relationship of the mandible 410 to the skull 400, especially to the temporal bone 406 that makes up the area around the ear. The head 412 of the mandible 410 sits in a bowl-shaped socket 408 of the temporal bone 406, forming the temporomandibular joint or TMJ. The head of the mandible 410 is separated from the temporal bone by a thin disk of cartilage and held in place by muscles and ligaments. Because of these unique structures, the TMJ allows much more movement than just the swinging action of a hinge joint. It allows the mandible to move forward and backwards several millimeters and allows the head 412 of the mandible 410 on one side, e.g., the left, to rotate while the head 412 of the mandible 410 on the other (right) side moves outward and forward, causing the jaw to move to the left, as in chewing. In normal daily activities, such as speech and mastication, the position of the mandible is determined not only by the activity of the muscles and TMJ, but also by the position and interaction of the teeth. However, when the person is sleeping, the mouth is generally open with the teeth disengaged, and the musculature and joint structure determine the position. For a person lying on their back, the mandible can relax into its most posterior position, allowing maximal contact between the posterior tongue and the nearby soft structures.

The oral appliances used for mandibular advancement position the mandible forward during sleeping, as shown in FIG. 4B. Although the differences are somewhat subtle, note that in the normal dentition shown, the lower incisors 420 (front teeth) move in front of the upper incisors 422, while the head 412 of the mandible 410 rides up the anterior side of the socket 408 of the temporal bone. This movement pulls the tongue forward, maintaining a clear space behind the tongue for breathing.

Studies have shown that mouthpieces providing mandibular advancement are as effective as CPAP in maintaining an open airway. This has been verified in unconscious patients whose musculature had been paralyzed, confirming that this is due to anatomical relationships and that the results do not require muscle activity. There are a number of versions of this type of mouthpiece. Some are custom-made, while others are of the "boil and bite" variety used in many school athletic programs. Although mandibular advancement was originally not well accepted by the medical community, the results of scientific studies are bringing this methodology into greater favor. However, as with CPAP, even when the devices work, many patients cannot tolerate the intra-oral devices. In other cases, the patient may tolerate the mouthpiece, only to find that the pressure exerted on the teeth by the appliance causes the teeth to shift out of position.

As an example of this problem, one of the inventors of the present application was diagnosed with severe sleep apnea and placed in an intra-oral device to correct the problem. However, after four years of using the intra-oral device, he was unable to eat solid food and was rapidly losing weight because of it. An oral examination revealed that his anterior teeth touched, but his posterior teeth did not. It was realized at that point that the pressure of the oral appliance had caused his lower anterior teeth to rotate to a more forward position, while the upper anterior teeth rotated to a more posterior position, as shown in FIG. 5.

Thus, despite the large number of devices and methods for the treatment of snoring, there remains a need for an anti-snoring device and/or method that maintains an open pharyngeal airway, is well tolerated, and does not exert pressure on the teeth.

SUMMARY OF THE INVENTION

An extra-oral device is disclosed which can prevent snoring and sleep apnea in appropriate patients. The device consists of a headpiece, worn by the user while sleeping, with adjustable jaw pads that force the mandible to a protruded position. As shown in studies on intra-oral devices, this mandibular advancement results in an unobstructed airway and the cessation of snoring for many users. These benefits are incurred without the need to put pressure on the teeth, thereby preserving the normal dentition.

Additional aspects, features, embodiments, and advantages of the present invention will be set forth, in part, in the description that follows, or may be learned from practicing or using the present invention. The objects and advantages may be realized and obtained by the means of the features and combinations particularly pointed out throughout this description and the appended claims. It is to be understood that the foregoing description and the following detailed description are exemplary and explanatory only and are not to be viewed as being restrictive of the invention as claimed.

BRIEF DESCRIPTION OF THE DRAWINGS

The novel features believed characteristic of the invention are set forth in the appended claims. The invention itself, however, as well as a preferred mode of use, further objects and advantages thereof, will best be understood by reference to the following detailed description of an illustrative embodiment when read in conjunction with the accompanying drawings, wherein:

FIG. 4A shows the normal articulation of the mandible, while FIG. 4B shows the mandible in the forward position that has been shown to prevent snoring and apnea in many cases;

DETAILED DESCRIPTION OF THE DRAWINGS

Figure 6A:
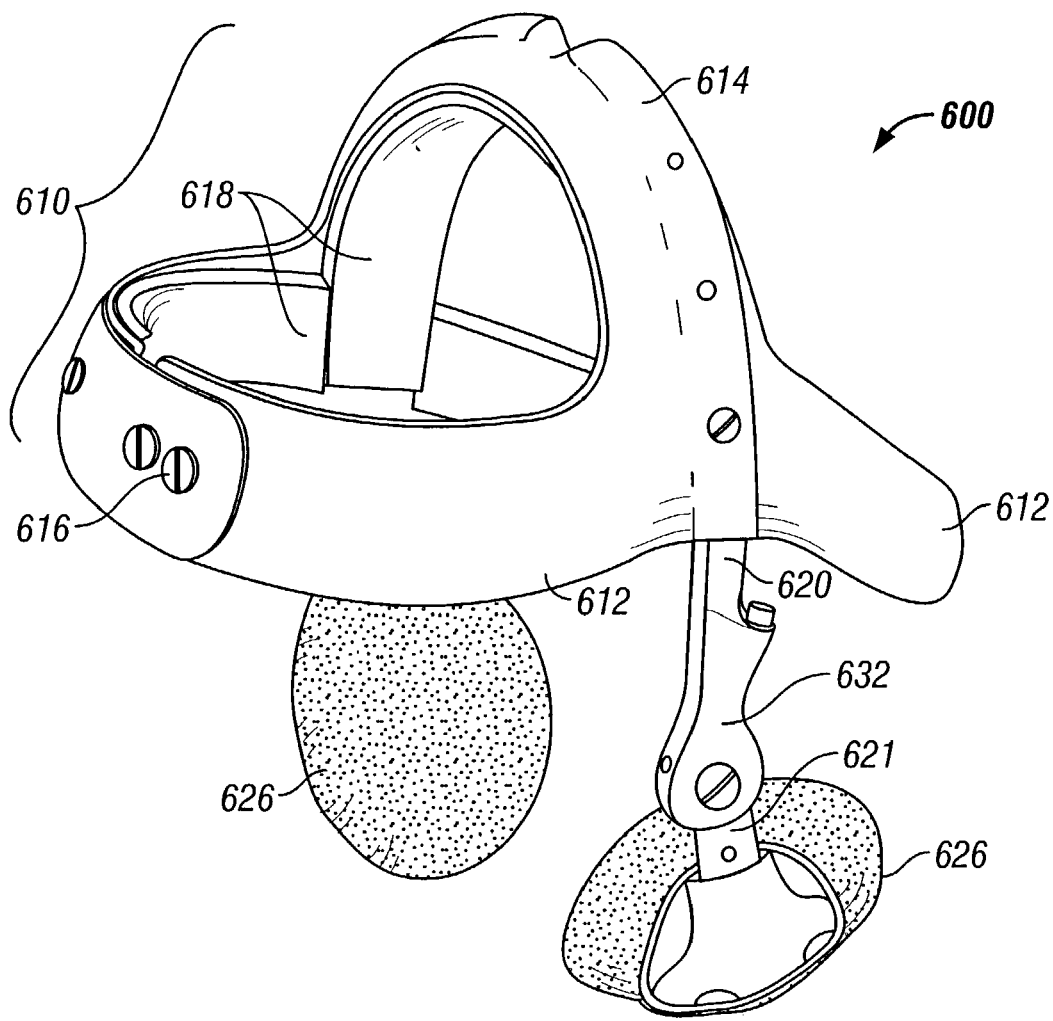
FIGS. 6A, 6B, and 6C are a perspective view, a frontal view, and a profile view respectively of one embodiment of the extra-oral anti-snoring device disclosed herein.
Figure 6B:
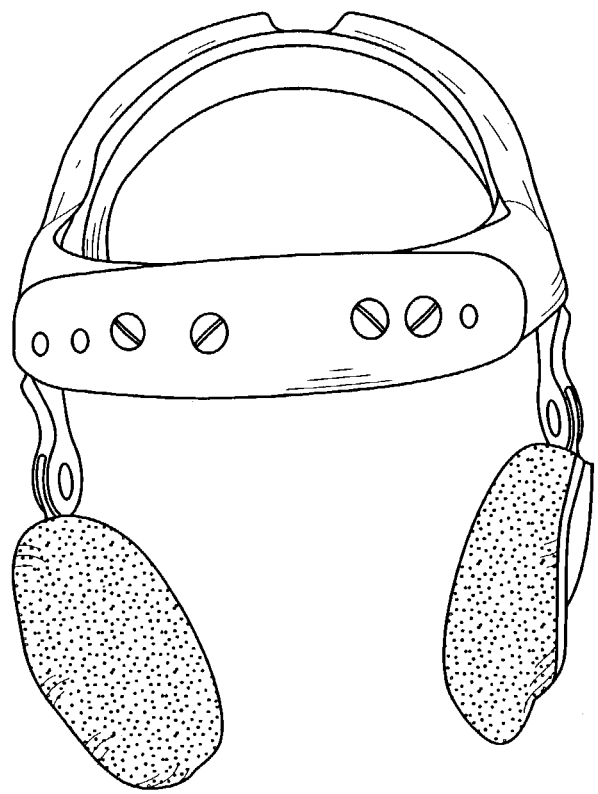
Figure 6C:
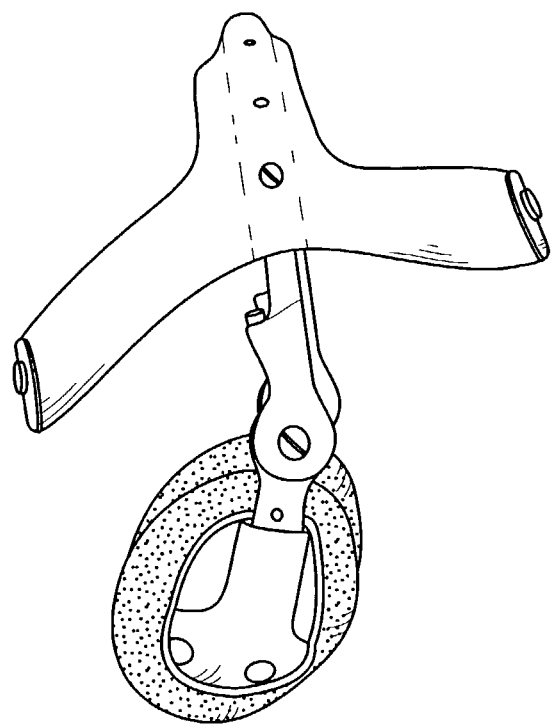

The inventive device will now be explained with reference to FIGS. 6A, 6B, and 6C. These drawings illustrate a perspective view, a frontal view, and a profile view respectively of a first embodiment of the anti-snoring device 600. Device 600 is comprised of a headpiece 610 joined to mandibular cradles 626 by a spring-action connector 632. Headpiece 610 is made from bands of a sheet metal and has both a headband 612 that encircles the head and a coronal piece 614 that extends across the crown of the head to connect the two sides of the headband 612. This headpiece is custom fitted to the user, as the framework must be fairly strong and must be rigid enough to withstand the forces necessary to displace the mandible. The inside of the headpiece is preferably lined with foam padding 618 to improve the comfort of the device. The mandibular cradles 626 are attached to headband 612 by metal connectors 620, 621, which are separated by a klenzak joint 632. Klenzak joints were originally developed to use with polio patients, providing a spring action at the ankles that rotates the toes upward during walking. It is used in this application to urge the mandible into position. The metal connectors 620, 621 are formed of 1/2-1/8" stock aluminum. Preferably the upper metal connector 620 runs all the way across the crown of the head to provide stability and is fastened to the headpiece by rivets or screws. The mandibular cradles 626 are metal and plastic structures, with a cushioned cover for comfort. In the presently preferred embodiment, the cushions are condylar pads, used in the manufacture of leg braces, although later models can be manufactured specifically for the jaw.

Figure 7:
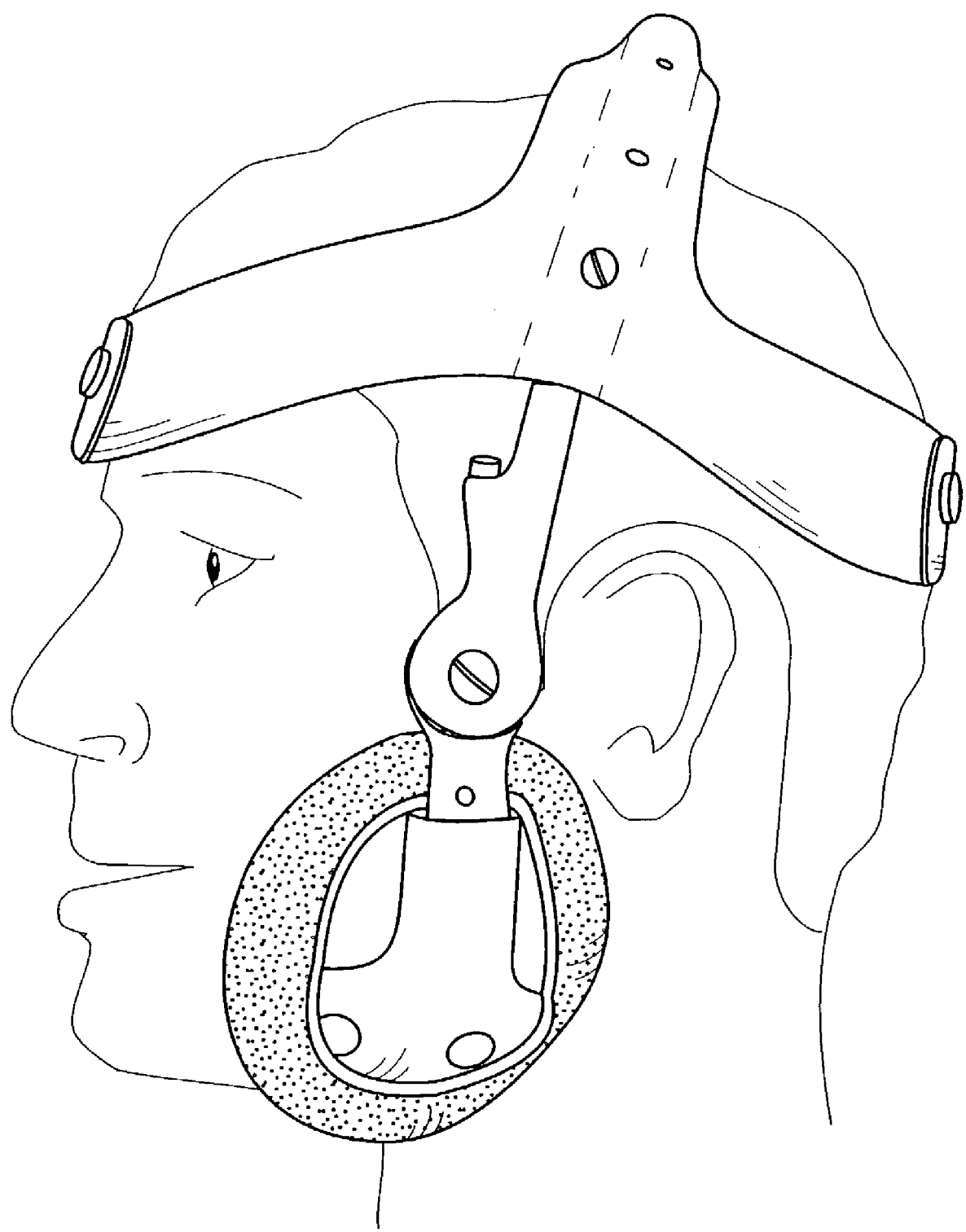
FIG. 7 shows the device of FIG. 6 in place on a user.

FIG. 7 shows the innovative anti-snoring device 600 in place on a user. The mandibular cradles 626 provide cradling of the angle of the mandible in a protruded position. In most persons, this will mean that their lower incisors will be positioned in front of their upper incisors, a reversal of the normal position. The anti-snoring device does not allow the mandible to slip into the relaxed position during sleep that allows snoring to happen, but maintains an open airway. When wearing the innovative device 600, it is desirable for the user to also wear a mouth guard 650. Unlike the mouth guards used to provide mandibular advancement, the mouth guard shown puts no pressure on the teeth. Rather, the mouth guard 650 provides a small amount of opening between the upper and lower teeth and prevents interfering contacts that can induce the shifting of teeth and/or jaw pain. The mandibular cradles strongly urge the jaw forward, but do not prevent all movement of the mandible.

Manufacture

Figure 1A:
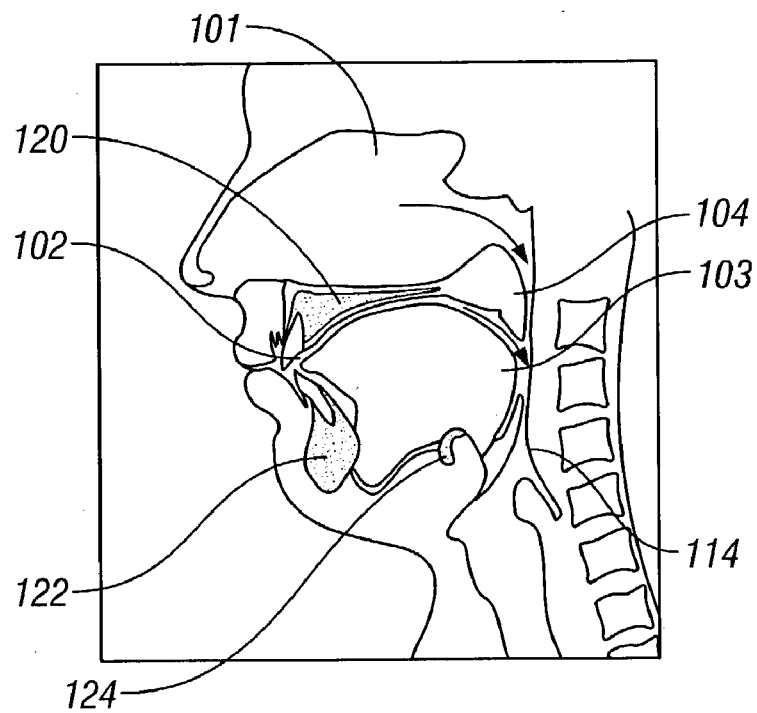
FIGS. 1A and 1B are views of the upper respiratory tract, demonstrating some of the anatomical features involved in snoring.
Figure 1B:
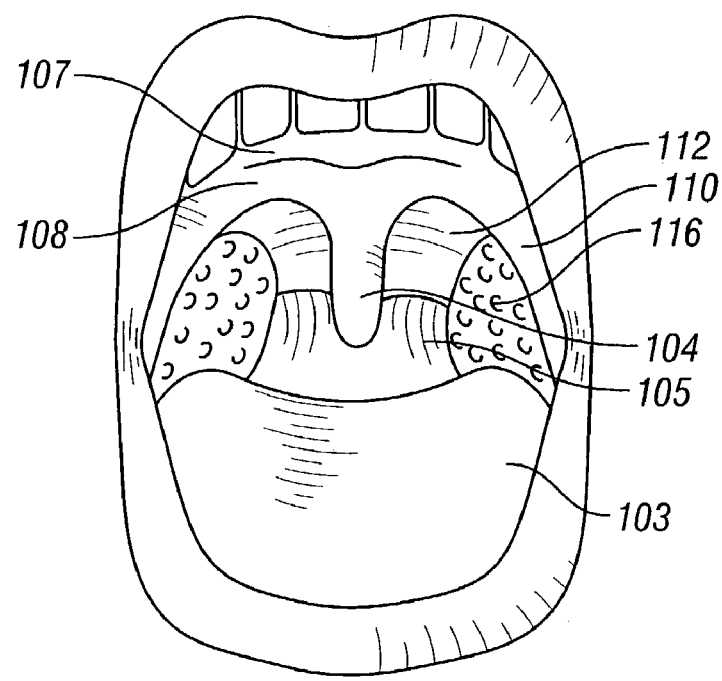
Figure 2:
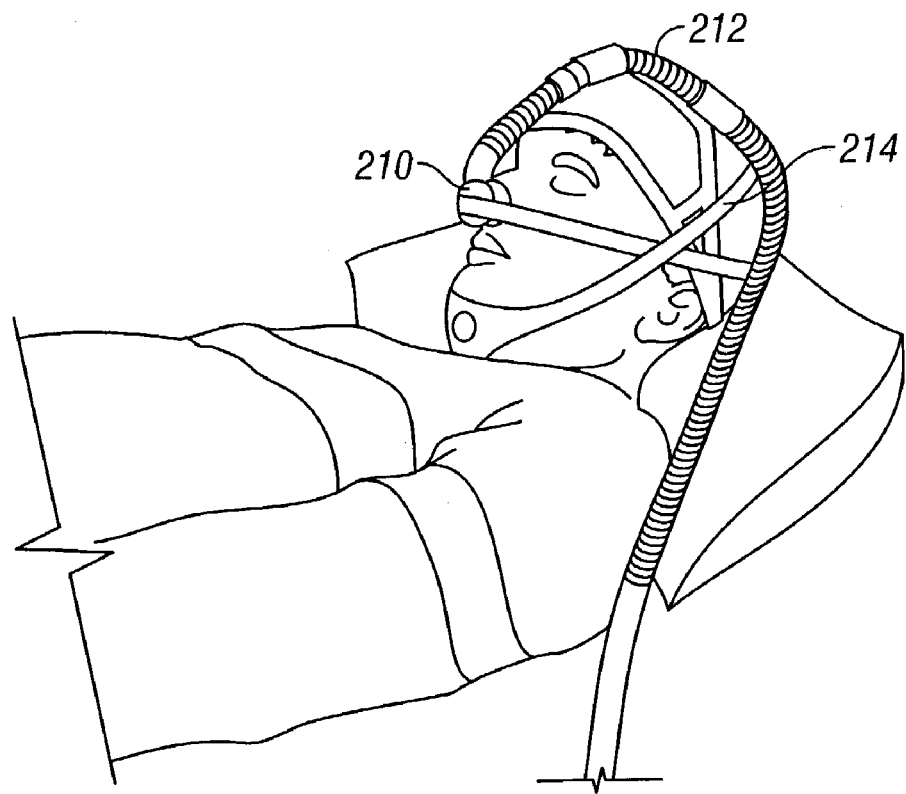
FIG. 2 illustrates a sleeper using a CPAP machine.
Figure 3:
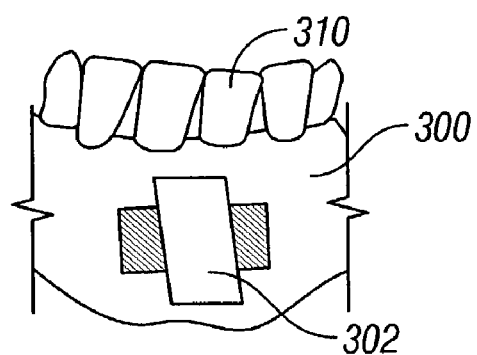
FIG. 3 demonstrates a surgical procedure to prevent snoring and apnea.
Figure 4A:
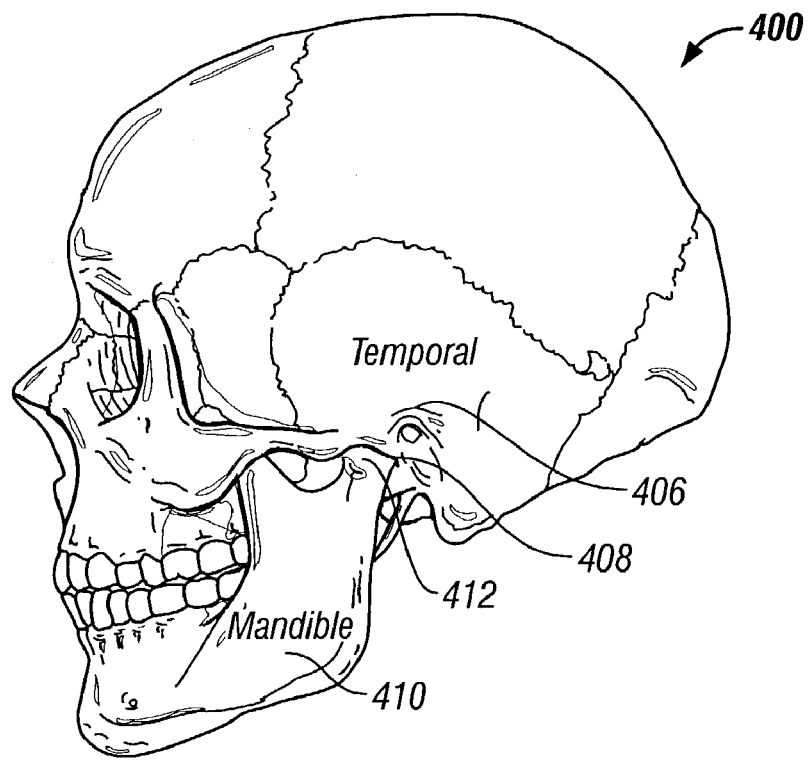
FIGS. 4A and 4B are views of the bones of the skull.
Figure 4B:
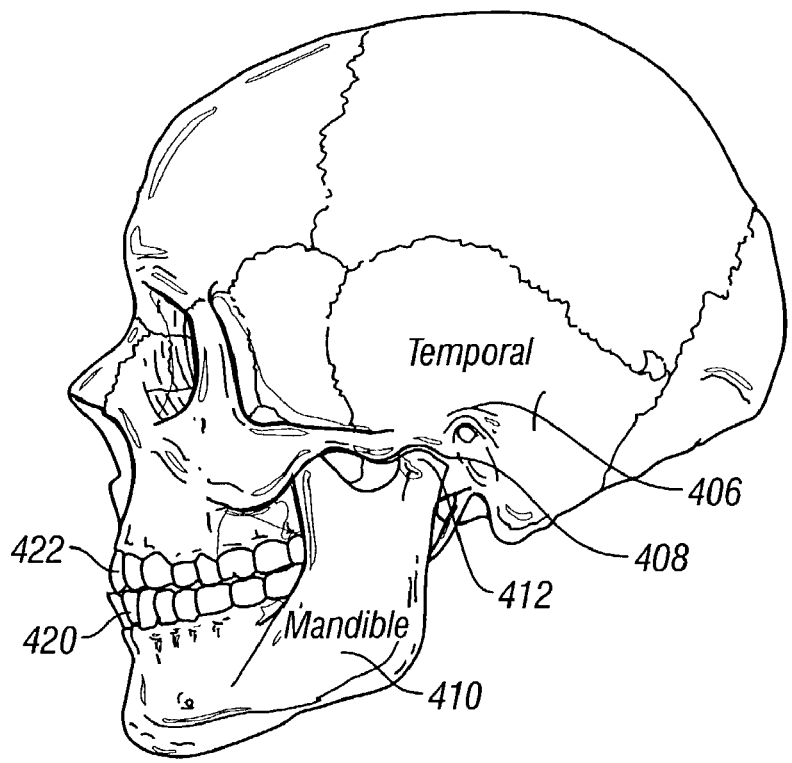
Figure 5:
FIG. 5 shows the rotation of the anterior teeth caused by an intra-oral appliance for sleep apnea.
Figure 8:
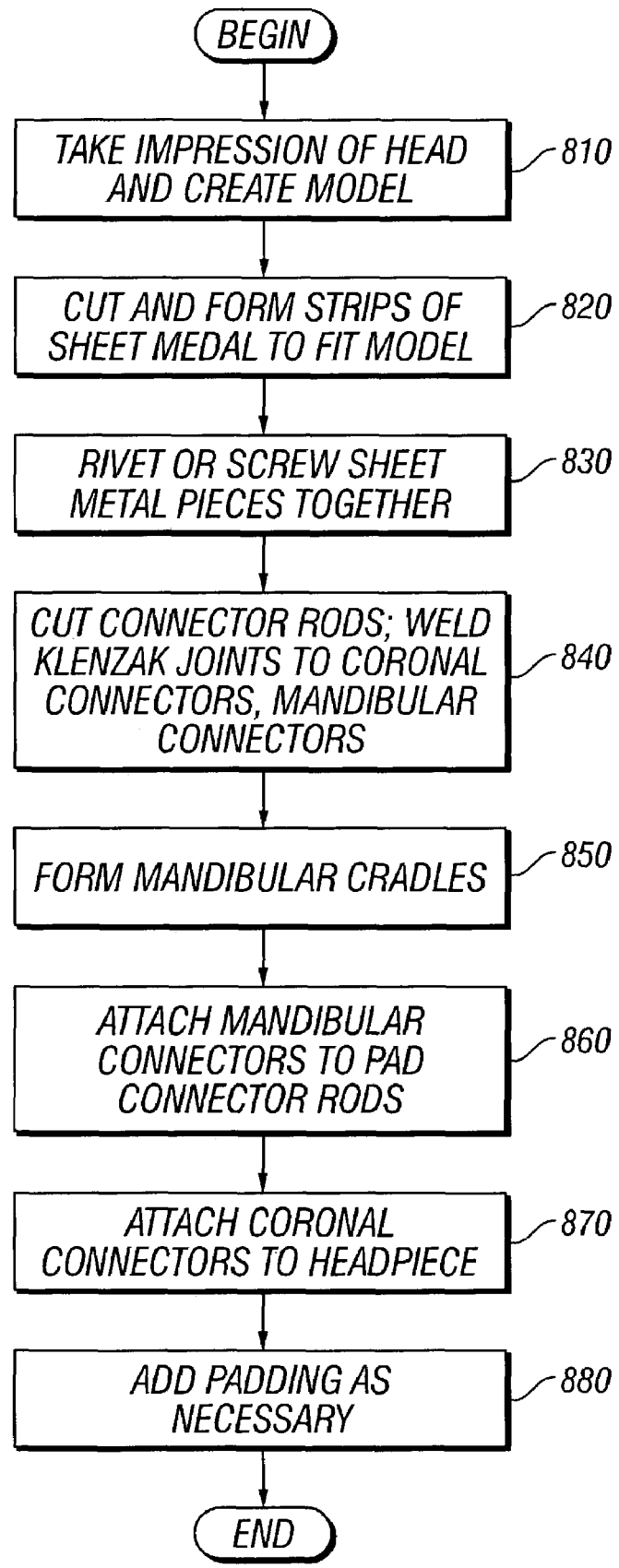
FIG. 8 shows a flowchart of the process of making the innovative device.

As mentioned above, the mandibular advancement device is custom-made, much as are leg braces, and they have developed out of some of the same technology. FIG. 8 illustrates the method used to make the embodiment illustrated in FIGS. 6 and 7. To make the device, plaster can be used to make an impression of the head and the impression is used to create a model of the head (step 810). The headpiece is then formed. Strips of sheet metal approximately 1½" wide are shaped on the mold to form a structure like that of FIGS. 2A-C (step 820). The strips can then be fastened together with rivets or screws to hold the pieces stably together (step 830). The metal connectors 620, 621 are of ½ by ⅛" stock aluminum, which are easily bent along the narrow dimension. Appropriate lengths are bent to conform to the mold of the head, with the coronal connector 620 spanning the crown of the head and shorter mandibular connectors 621 sized to join the klenzak joint 632 to the mandibular cradles 626. The connectors 620, 621 are then welded to the klenzak joints 632 (step 840). Meanwhile, the mandibular cradles have been formed by vacuum molding sheets of plastic to conform to the mold of the user's jaw line (step 850). The plastic can be polyethylene or polypropylene in the range of ⅛-¼" thick, preferably 3/16". The mandibular cradles are trimmed and smoothed, then attached to the mandibular connectors 621 (step 860) by rivets or screws. The upper connectors 620, with attached mandibular cradles, are attached to the headpiece by rivets or screws (step 870). Finally, padding is added (step 880). The pads in the mandibular cradles are currently made of air-filled cushions and are borrowed again from the technology of leg braces, where they are used as condylar pads. Thin strips of foam are also added on the inside of the headpiece for cushioning and to make up for minor inconsistencies between the mold and the user.

Alternate Embodiment

Figure 9A:
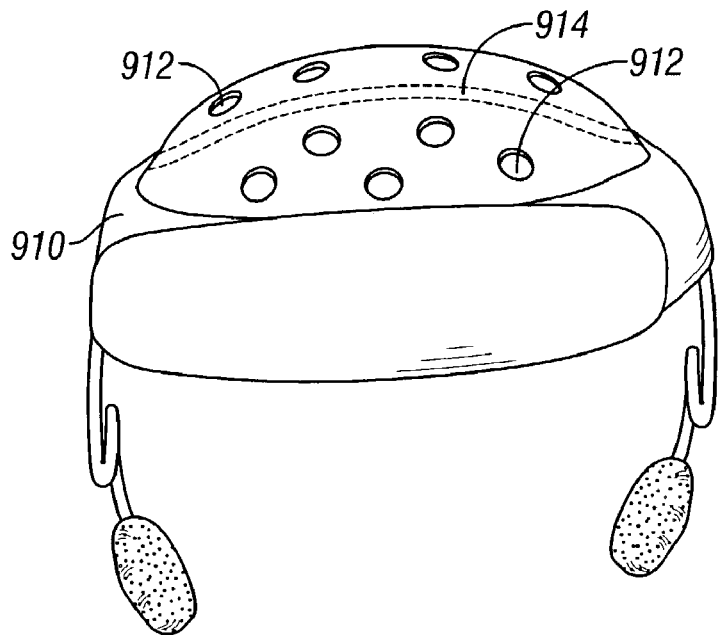
FIGS. 9A and 9B illustrate an alternate embodiment of a device made according to the invention.
Figure 9B:
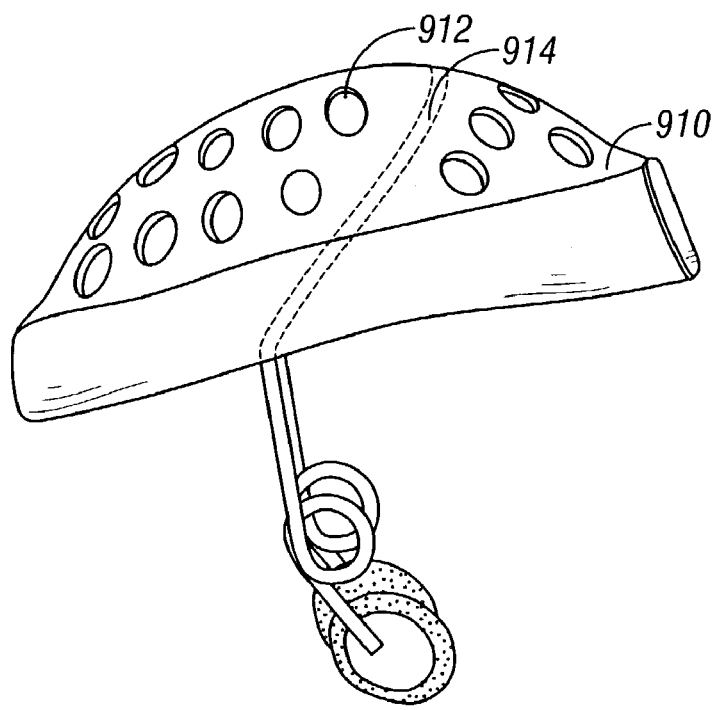

FIGS. 9A and 9B illustrate an alternate embodiment, which will be explained to show some of the ways in which the device and method explained above can be modified. In this embodiment, the headpiece 910, as well as the mandibular cradles 920, is made of plastic, with air holes 912 for ventilation. The coronal connector 914 and the mandibular connectors 916 are formed of a heavy gauge wire, with a coiled portion of the same wire forming a heavy spring joint 918.

Figure 10A:
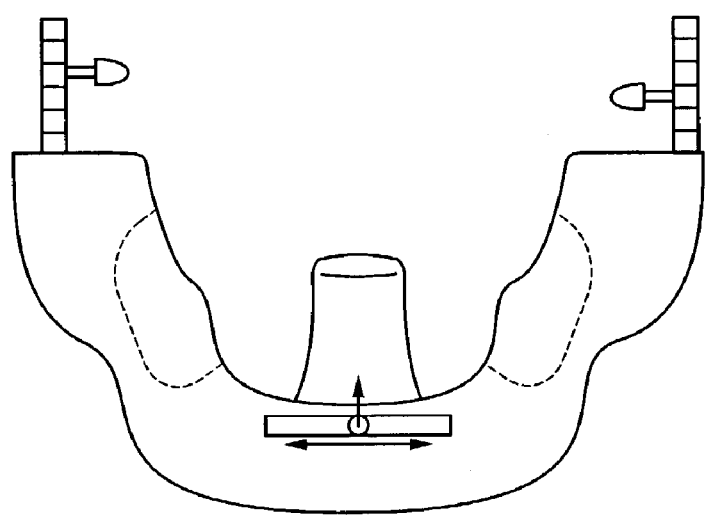
FIG. 10A shows an impression device that can be used to take impressions of the angles of the jaw while capturing their relationship to both the ears and the upper teeth.
Figure 10B:
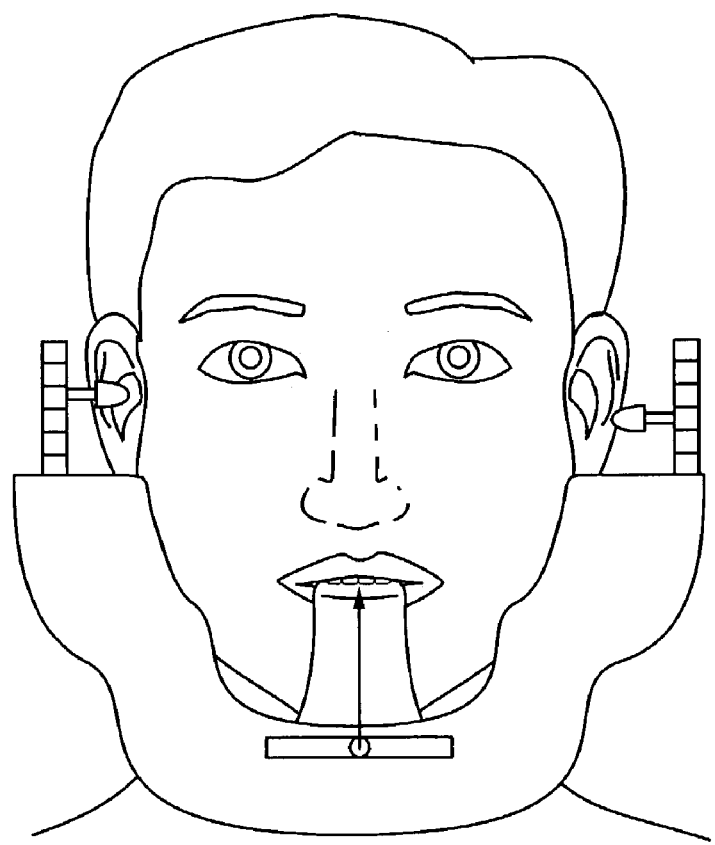
FIG. 10B shows the impression device 1010 as it is capturing the impression of the angles of the jaw on a patient.
Figure 11:
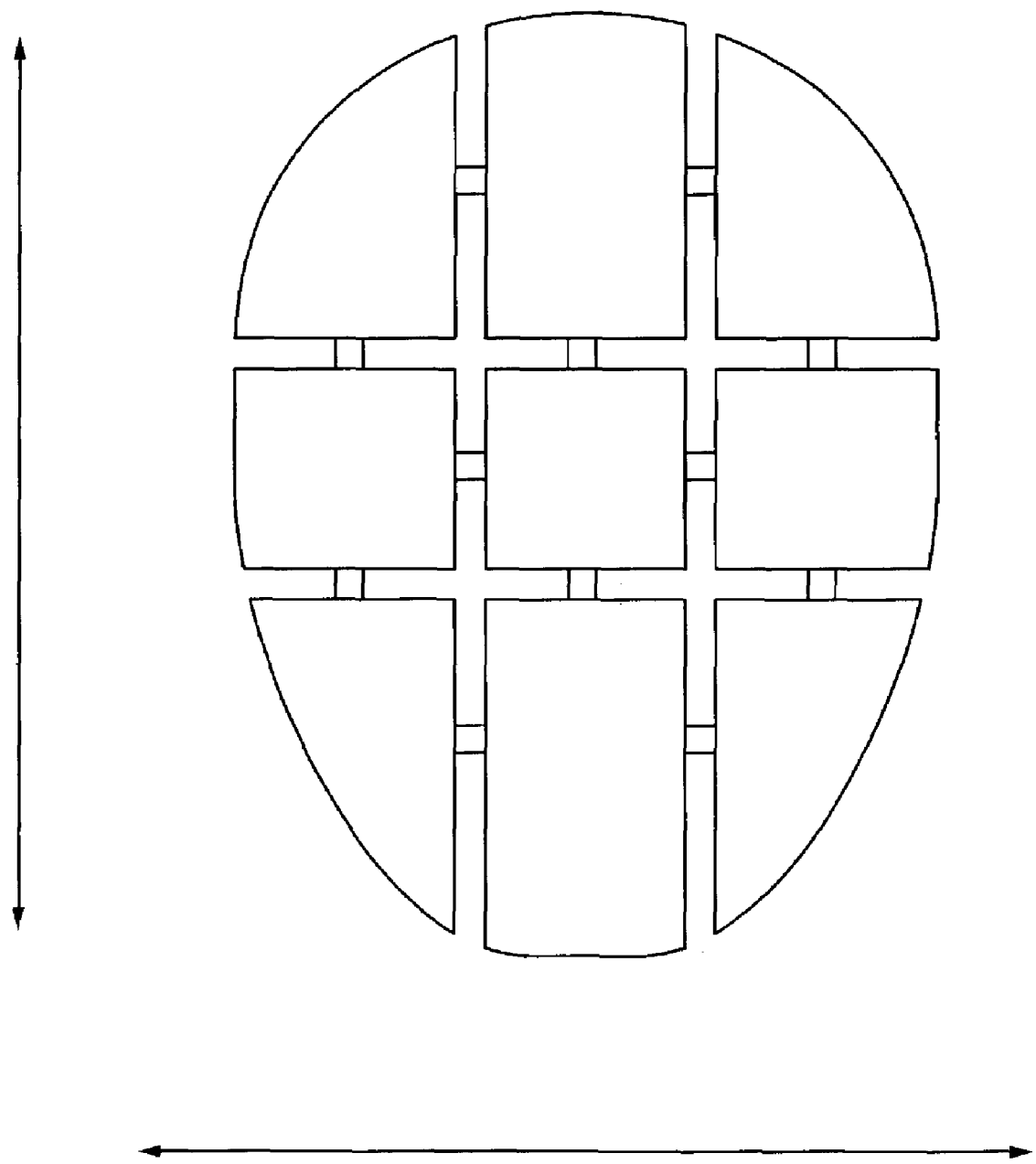
FIG. 11 shows a framework model of the upper head that contains nine separate sections, which can be adjusted much as a dressmaker's dummy.

In forming the model in this embodiment, rather than taking a plaster mold of the head, two separate impressions are taken: first, the top of the head and second, the angle of the mandible. An impression of the top of the head can be taken in alginate (a material used in making dental impressions), using one of a set of molds sized to an approximate fit. The location of the ears can be marked on the impression and transferred to the model made from this mold. FIG. 10A shows an impression device 1010 that can be used to take impressions of the angles of the jaw, while capturing their relationship to both the ears and the upper teeth, thus capturing them in three-dimensional space. The device 1010 has earplugs 1012 that fit into the ear. These earplugs 1012 are preferably adjustable in both the horizontal and vertical directions. A bite plate 1014 is held between the upper and lower teeth and a midline captured. Hollows 1016 in device 1010 at the angle of the jaw can hold alginate impression material to capture the shape of the angle of the jaw. FIG. 10B shows the impression device 1010 as it is capturing the impression of the angles of the jaw on a patient.

Once models are made of the head and angle of the mandible, the connectors can be shaped to the model of the head. In this embodiment, the connectors angle forward approximately 45° at the lower edge of the headpiece to better distribute the pressure that is used to force the mandible forward.

The headpiece and mandibular cradles are then formed. Sheets of plastic, preferably polyethylene or polypropylene in the range of 1/8-1/4" thick, are vacuum formed over the models of the head and angles of the mandible. The coronal connector can be tacked into position on the model before the plastic is shaped, so that the headpiece has a groove for the connector to fit into. Once shaped, the headpiece and mandibular cradles are trimmed, air holes for venting are formed in the headpiece, and the pieces are smoothed. The coronal connector is then fastened to the headpiece using rivets or screws and the mandibular cradles are similarly attached to the mandibular connectors. Finally, padding will be added.

Further Alternate Embodiment

Figure 12A:
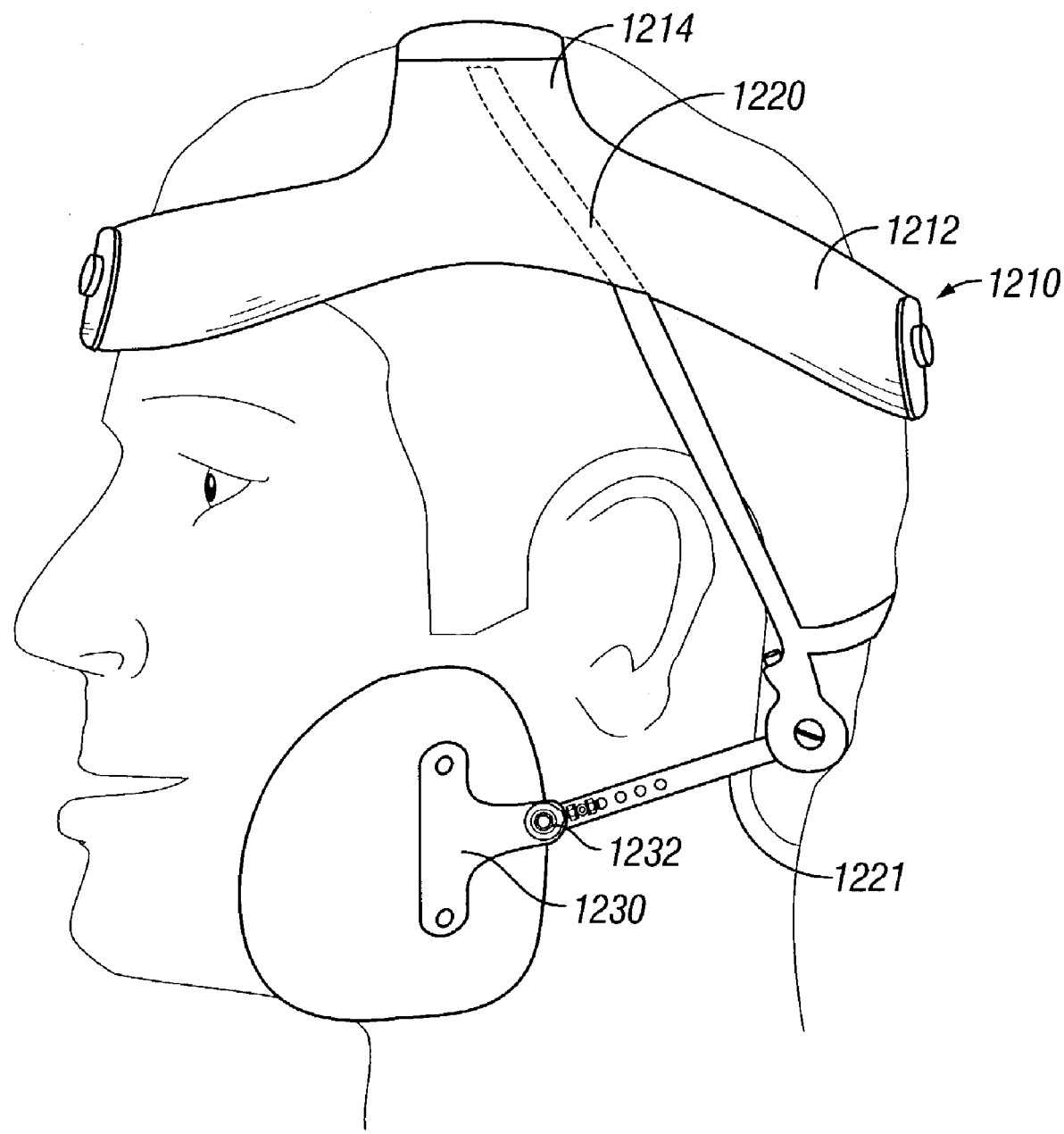
FIGS. 12A and 12B show a further alternate embodiment of the invention and a detail of the hardware joining the mandibular cradles to the headgear.
Figure 12B:
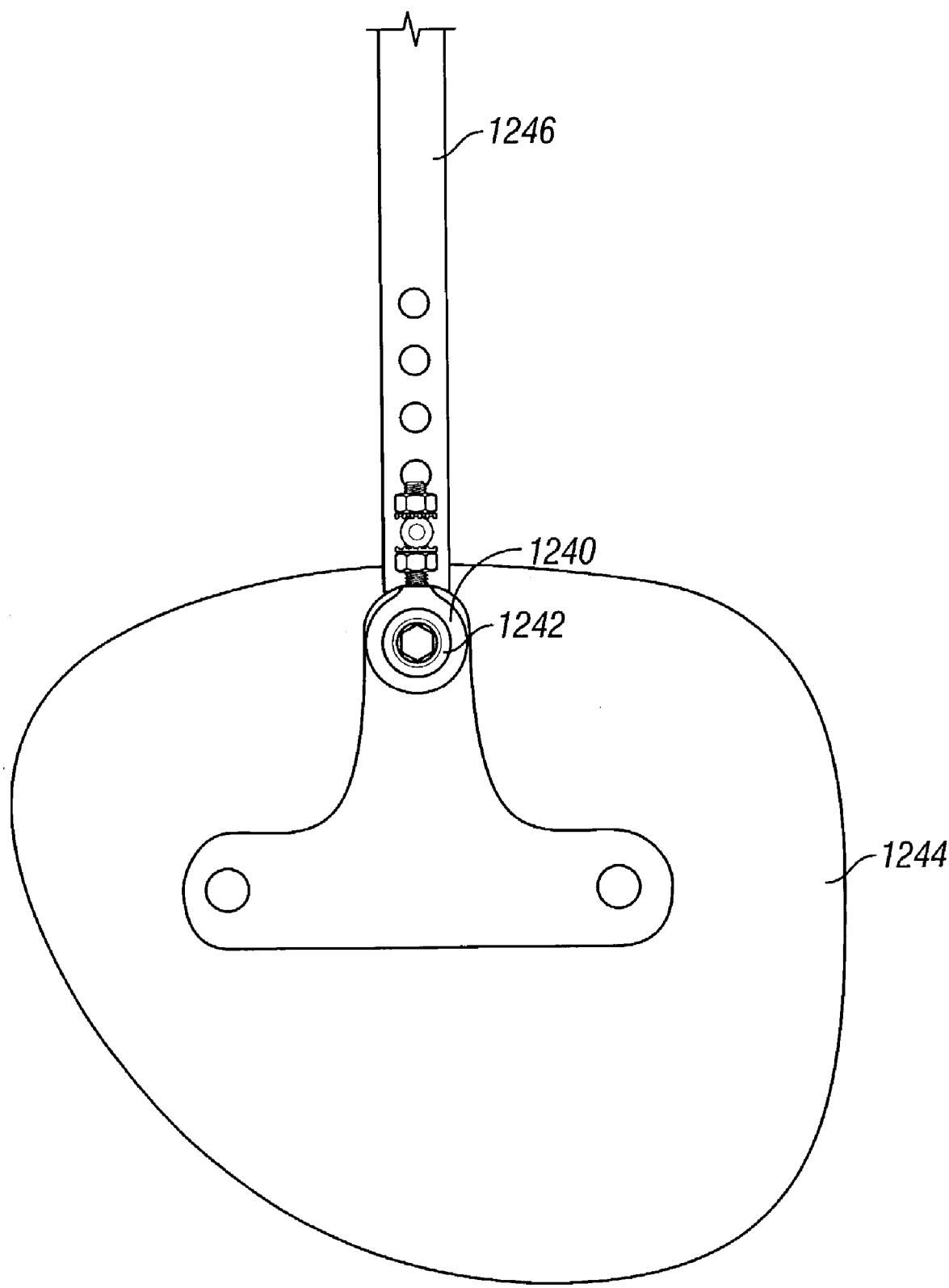

A further alternate embodiment is shown in FIGS. 12A and 12B. In this embodiment, the headpiece 1210 is adjustable, with adjustments possible in both the headband 1212 and the coronal piece 1214. The coronal piece 1214, as well as the coronal connector 1220 that it contains, form an acute angle with the front portion of the headband 1212. This helps take some of the pressure off of the forehead during use.

In this embodiment, the coronal connectors 1220 exit the headpiece behind the ears, to provide pressure against the mandible in a more favorable direction. Again, a Klenzak joint provides the connection between the coronal connectors 1220 and the, mandibular connectors 1221. A metal plate 1230 is attached to the back of the mandibular cradles. The joint between this plate 1230 and the mandibular connector 1221 is provided by a captured ball-and-socket joint 1232. A close-up of the mandibular cradle and connector is shown in FIG. 12B. With this joint, the socket 1240 locks around the ball 1242 so that the mandibular cradle 1244 is securely fastened to the mandibular connector 1246 by the joint, yet the mandibular cradle 1244 is capable of adjusting in all three dimensions to the angle of the jaw. When the extra-oral device is fitted to a person, several small setscrews (not specifically shown) can be adjusted with an allen wrench to preserve the optimal setting of this joint and prevent movement of the joint during sleep. Because of the additional length of the mandibular connectors, a posterior connector provides additional stability, running across the back of the head.

Further Variations

Additional changes can be made to either the device or the method of making the device. In one alternate embodiment, an adjustable model of the top of the head is used to form the headpiece. FIG. 10 shows a framework model of the upper head that contains nine separate sections, which can be adjusted much as a dressmaker's dummy. In use, the framework would preferably be covered with a thin material that can help cover the gaps in the framework. Measurements are taken of the head, such as the circumference, the distance across the crown of the head from ear to ear, and the distance across the crown of the head from front to back. These measurements are used to set the model to the proper size; the headpiece can then be built on the model.

In an alternate embodiment, the headpiece for the appliance can have adjustable features built in, so that the headpiece need not be made to a specific mold, but can be of a more generic style, with the ability to adjust the size of the headpiece and the location of the mandibular cradles in relationship to the headpiece.

In an alternate embodiment, the coronal connector is attached to the headpiece behind the ear, rather than in front of the ear. This gives a different angle for the application of force to the mandible.

In an alternate embodiment, the forward force is provided, not by a klenzak joint, but by a heavy spring coil that resists attempts of the mandible to move posterior. This spring coil is preferably formed of 1/8" piano wire.

It is noted that the inventors have found a need to have a rigid framework, in order to provide the necessary force to hold the mandible in its forward position. Other details can vary to meet the desirable qualities of comfort, cost, and availability.

The description of the present invention has been presented for purposes of illustration and description, and is not intended to be exhaustive or limited to the invention in the form disclosed. Many modifications and variations will be apparent to those of ordinary skill in the art. The embodiment was chosen and described in order to best explain the principles of the invention, the practical application, and to enable others of ordinary skill in the art to understand the invention for various embodiments with various modifications as are suited to the particular use contemplated.

We claim:

1. A method for preventing snoring and sleep apnea in a person, comprising the steps of:
    removably seating a rigid framework on the head of the person;
    adjusting a pair of mandibular cradles attached to said framework so that said pair of mandibular cradles exert a force on the mandible of the person sufficient to maintain the mandible in a protruded position relative to the maxilla.
2. The method of claim 1, wherein said seating step comprises activating a spring coil.

* * * * *